(12) United States Patent
Feldkamp et al.

(10) Patent No.: US 8,207,394 B2
(45) Date of Patent: Jun. 26, 2012

(54) INDUCTION COIL WETNESS SENSOR FOR AN ABSORBENT ARTICLE

(75) Inventors: Joseph Raymond Feldkamp, Appleton, WI (US); Jeffrey Robert Heller, Neenah, WI (US); Shawn Jeffery Sullivan, Neenah, WI (US); Sudhanshu Gakhar, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 817 days.

(21) Appl. No.: 11/983,970

(22) Filed: Nov. 13, 2007

(65) Prior Publication Data

US 2009/0124990 A1    May 14, 2009

(51) Int. Cl.
*A61F 13/15* (2006.01)
(52) U.S. Cl. ........ 604/361; 604/358; 604/362; 128/886; 200/61.04; 200/61.05; 340/603; 340/604; 340/605
(58) Field of Classification Search .................. 604/358, 604/361, 362
See application file for complete search history.

(56) References Cited

U.S. PATENT DOCUMENTS

| | | | |
|---|---|---|---|
| 4,800,370 A | | 1/1989 | Vetecnik |
| 4,931,893 A | * | 6/1990 | Glennon et al. ................ 361/45 |
| 5,463,377 A | | 10/1995 | Kronberg |
| 6,677,859 B1 | | 1/2004 | Bensen |
| 2004/0064114 A1 | | 4/2004 | David et al. |
| 2004/0133801 A1 | | 7/2004 | Pastorelli et al. |
| 2006/0244614 A1 | | 11/2006 | Long et al. |
| 2007/0024457 A1 | | 2/2007 | Long et al. |
| 2007/0049881 A1 | | 3/2007 | Ales et al. |
| 2007/0142797 A1 | | 6/2007 | Long et al. |
| 2007/0252712 A1 | | 11/2007 | Allen et al. |
| 2008/0048786 A1 | | 2/2008 | Feldkamp et al. |

FOREIGN PATENT DOCUMENTS

EP          0 446 821 A2     1/1900

OTHER PUBLICATIONS

Hart, Lynn W. et al., "A Noninvasive Electromagnetic Conductivity Sensor for Biomedical Applications," *IEEE Transactions on Biomedical Engineering*, vol. 35, No. 12, Dec. 1988, pp. 1011-1022.

* cited by examiner

*Primary Examiner* — Tatyana Zalukaeva
*Assistant Examiner* — Ilya Y Treyger
(74) *Attorney, Agent, or Firm* — Randall W. Fieldhack

(57) ABSTRACT

A signaling device is provided for sensing and indicating the presence of a body exudate in an absorbent article, the device including a housing and a detection circuit disposed within the housing, the detection circuit including an induction coil and a marginal oscillator. A body exudate collection and detection system is also provided including an absorbent article and a signaling device adapted to be used in conjunction with the absorbent article, the signaling device including a housing and a detection circuit disposed within the housing, the detection circuit including an induction coil and a marginal oscillator. The signaling device can also include an attachment mechanism for removably attaching the housing to the absorbent article. The detection circuit can also include an electrical common and a conductor in electrical communication with the electrical common and with the body exudate.

19 Claims, 6 Drawing Sheets

INDUCTION COIL WETNESS SENSOR FOR AN ABSORBENT ARTICLE

BACKGROUND

Absorbent articles such as diapers, training pants, incontinence products, feminine hygiene products, swim undergarments, and the like, conventionally include a liquid permeable body-side liner, a liquid impermeable outer cover, and an absorbent structure. The absorbent structure is typically located between the outer cover and the liner for taking in and retaining liquids (e.g., urine) exuded by the wearer. The absorbent structure can be made of, for instance, superabsorbent particles. Many absorbent articles, especially those sold under the trade name HUGGIES™ by the Kimberly-Clark Corporation, are so efficient at absorbing liquids that it is sometimes difficult to tell whether or not the absorbent article has been insulted with a body exudate, especially when the absorbent article is being worn by a newborn or other very young wearers. Insult amounts in such wearers tend to be very small. Other wearers might also produce very small insults.

Accordingly, various types of moisture or wetness indicators have been suggested for use in absorbent articles. The wetness indicators include various passive indicators such as indicator strips, printing, or other devices within each absorbent article, requiring a caregiver to pay for the wetness indicator in each absorbent article whether or not the caregiver intends to use the wetness indicator. Wetness indicators may also include alarm devices that are designed to assist parents or attendants in identifying a wet diaper condition early on. These devices produce either a visual or an audible signal. Many of these devices rely on electronics, including conductive elements within each absorbent article that may increase the expense of the absorbent article.

Problems, however, have been encountered in designing a signaling device that can be used as desired but that does not appreciably increase the cost of each absorbent article, while providing a meaningful signal to the caregiver. In addition, passive indicators located adjacent the outer cover of an absorbent article allow a caregiver to recognize when the absorbent article has been insulted, but such indicators typically require sufficient liquid to soak through the entire absorbent structure of the absorbent article to reach the indicator on the inside of the outer cover before an indication can be produced.

SUMMARY

The present inventors undertook intensive research and development efforts with respect to improving absorbent articles, particularly in providing a wetness indicator only when desired by a caregiver and without adding to the cost of an absorbent article. A need exists for wetness detection in diapers and incontinence products in general. Technology that can be implemented without altering diaper construction is preferred.

A noninvasive induction type sensor measures electrical conductivity at some depth within an absorbent article. A useful approach is an induction coil conductivity sensor, which can be attached to an appropriate target zone on the outer cover of the absorbent article. The induction coil, forming part of a resonant circuit, experiences an impedance change when conductive liquid is placed nearby. This impedance change is detected in a marginal oscillator circuit, with its output interpreted to reflect a wetness level.

A signaling device is provided for sensing and indicating the presence of a body exudate in an absorbent article, the device including a housing and a detection circuit disposed within the housing, the detection circuit including an induction coil and a marginal oscillator. A body exudate collection and detection system is also provided including an absorbent article and a signaling device adapted to be used in conjunction with the absorbent article, the signaling device including a housing and a detection circuit disposed within the housing, the detection circuit including an induction coil and a marginal oscillator. The signaling device can also include an attachment mechanism for removably attaching the housing to the absorbent article. The detection circuit can also include an electrical common and a conductor in electrical communication with the electrical common and with the body exudate.

BRIEF DESCRIPTION OF THE DRAWINGS

The foregoing and other features and aspects of the present disclosure and the manner of attaining them will become more apparent, and the disclosure itself will be better understood by reference to the following description, appended claims and accompanying drawings.

Figure 1:
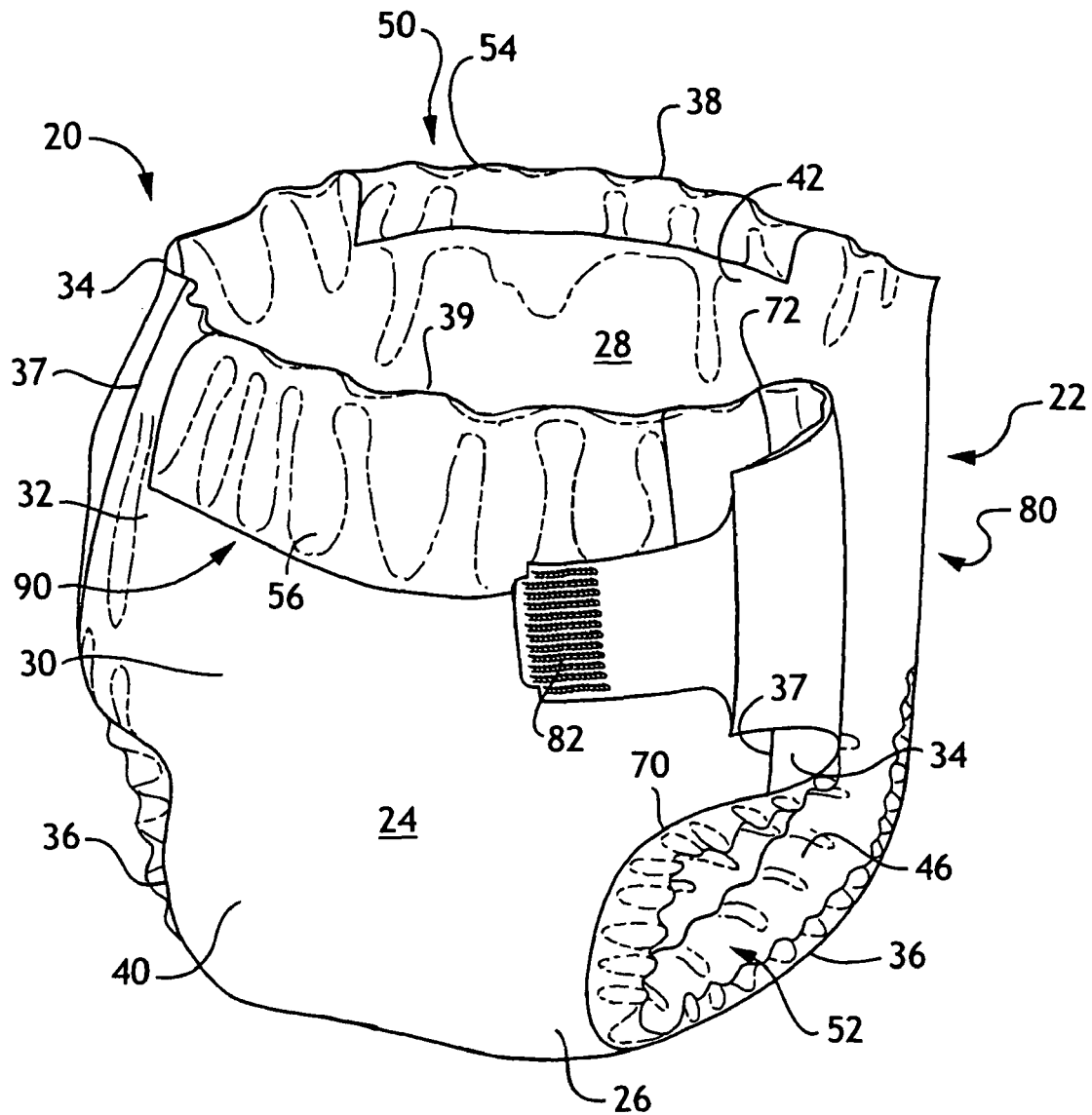
FIG. 1 is a rear perspective view of one aspect of an absorbent article.

Repeat use of reference characters in the present specification and drawings is intended to represent the same or analogous features or elements of the present disclosure.

DETAILED DESCRIPTION

It is to be understood by one of ordinary skill in the art that the present discussion is a description of exemplary aspects only, and is not intended as limiting the broader aspects of the present disclosure.

The present disclosure is generally directed to absorbent articles adapted to indicate the presence of a body exudate in the absorbent article or other changes in the condition of the product or wearer. The absorbent article may be, for instance, a diaper, a training pant, an incontinence product, a feminine hygiene product, a medical garment, a bandage, or the like. Generally, the absorbent articles are disposable, meaning that they are designed to be discarded after a limited use rather than being laundered or otherwise restored for reuse.

The present disclosure is directed to a body exudate indicating system used in conjunction with a disposable absorbent article 20. When the absorbent article 20 is insulted with a liquid, such as urine, menses, blood, or the like, the absorbent structure 44 captures and retains the liquid. Conventional absorbent articles 20 are so effective at retaining liquid that caregivers may not know when an absorbent article 20 has been insulted. With traditional products the caregiver does not have any way of determining whether the absorbent article 20 has been insulted, especially with younger wearers of the absorbent article 20 because insults from younger wearers tend to be quite small. The signaling device 110 is in electromagnetic communication with the absorbent structure 44, which addresses these issues.

Figure 2:
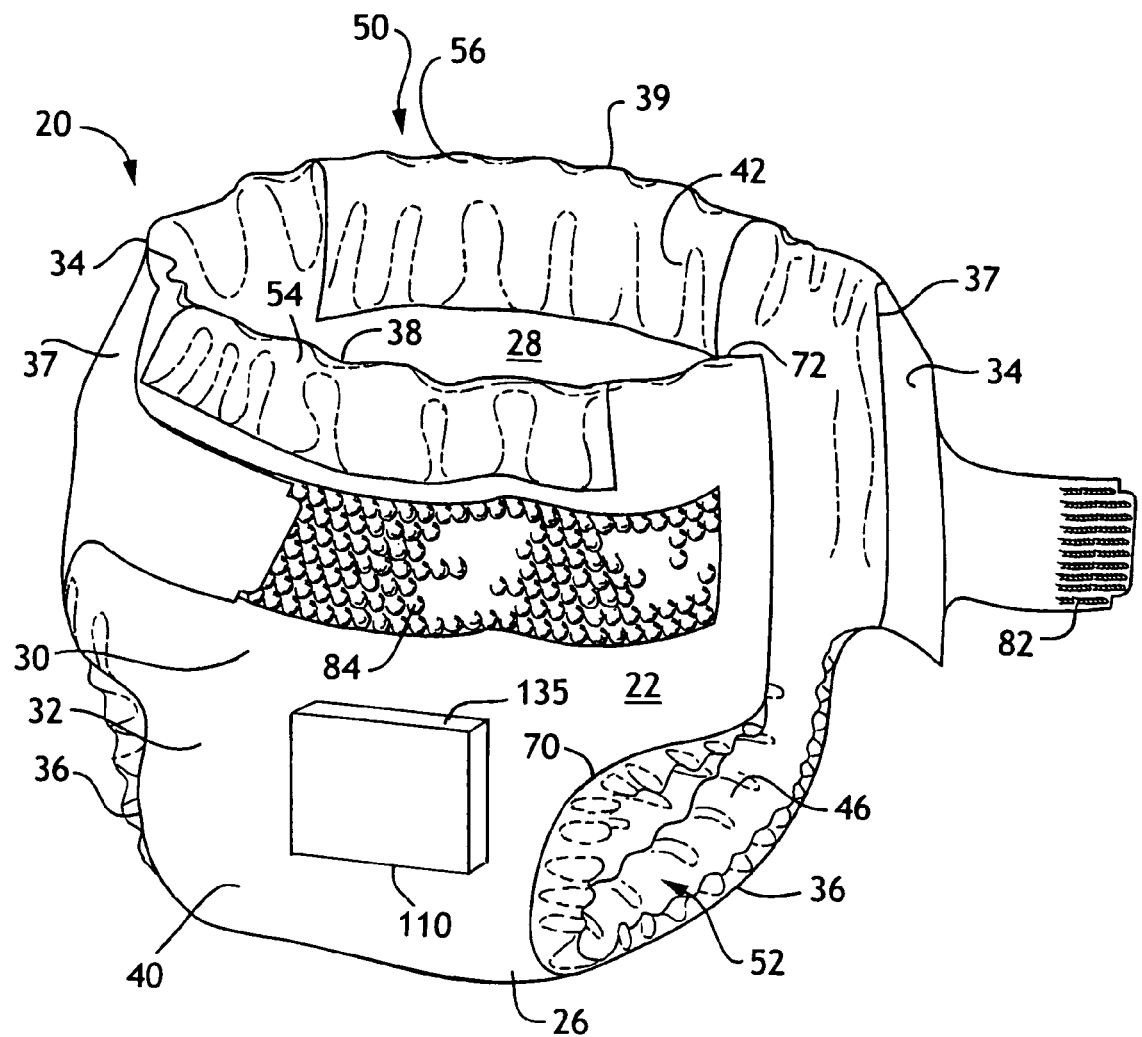
FIG. 2 is a front perspective view of the absorbent article illustrated in FIG. 1 including one aspect of a wetness indicator of the present disclosure.

Referring to FIGS. 1 and 2, for exemplary purposes, an absorbent article 20 that may be made in accordance with the present disclosure is shown. The absorbent article 20 may or may not be disposable. It is understood that the present disclosure is suitable for use with various other absorbent articles intended for personal wear including, but not limited to, diapers, training pants, swim pants, feminine hygiene products, incontinence products, medical garments, surgical pads and bandages, other personal care or health care garments, and the like, without departing from the scope of the present disclosure.

Figure 3:
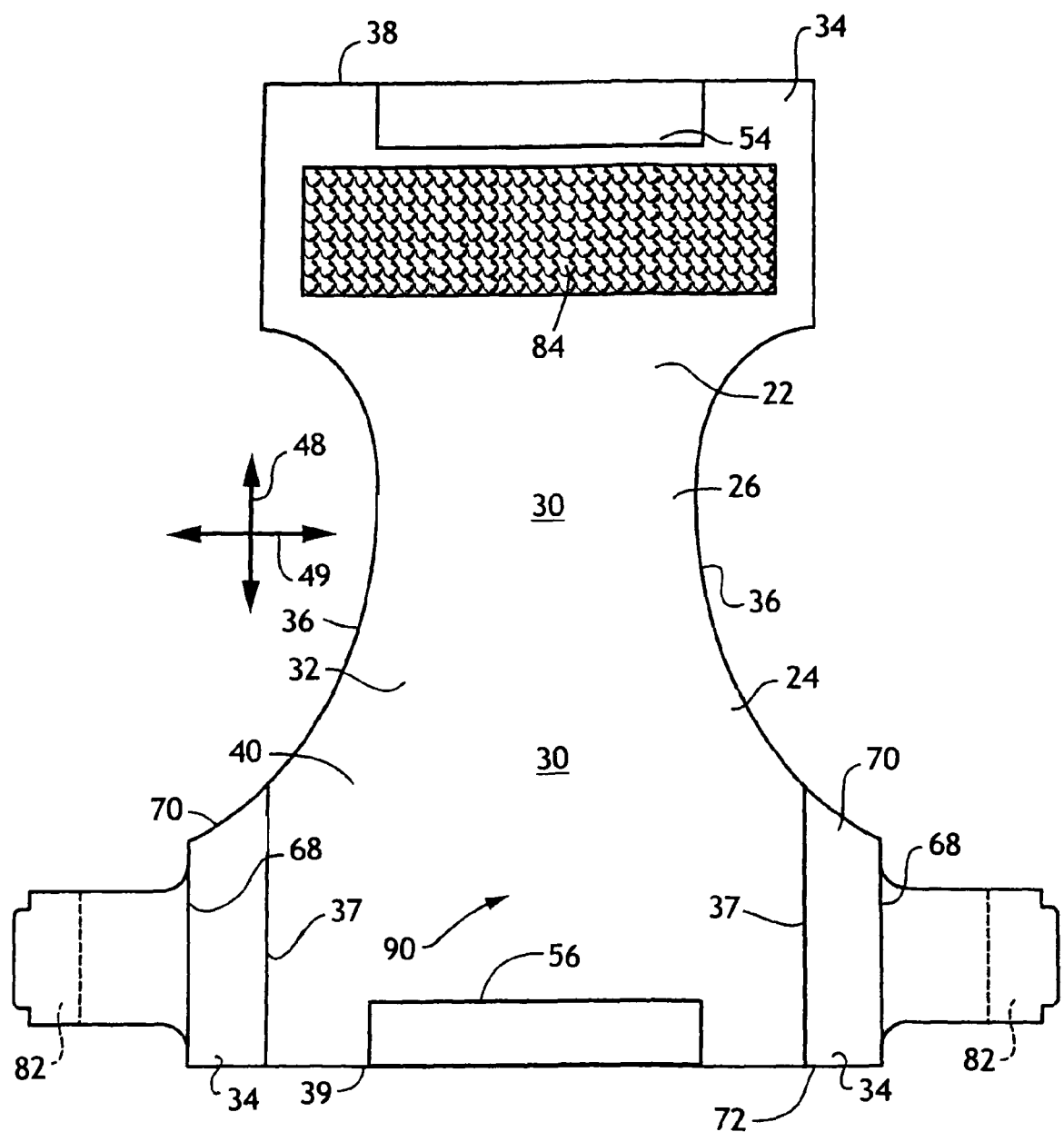
FIG. 3 is a plan view of the absorbent article shown in FIG. 1 with the article in an unfastened, unfolded and laid flat condition showing the surface of the article that faces away from the wearer.
Figure 4:
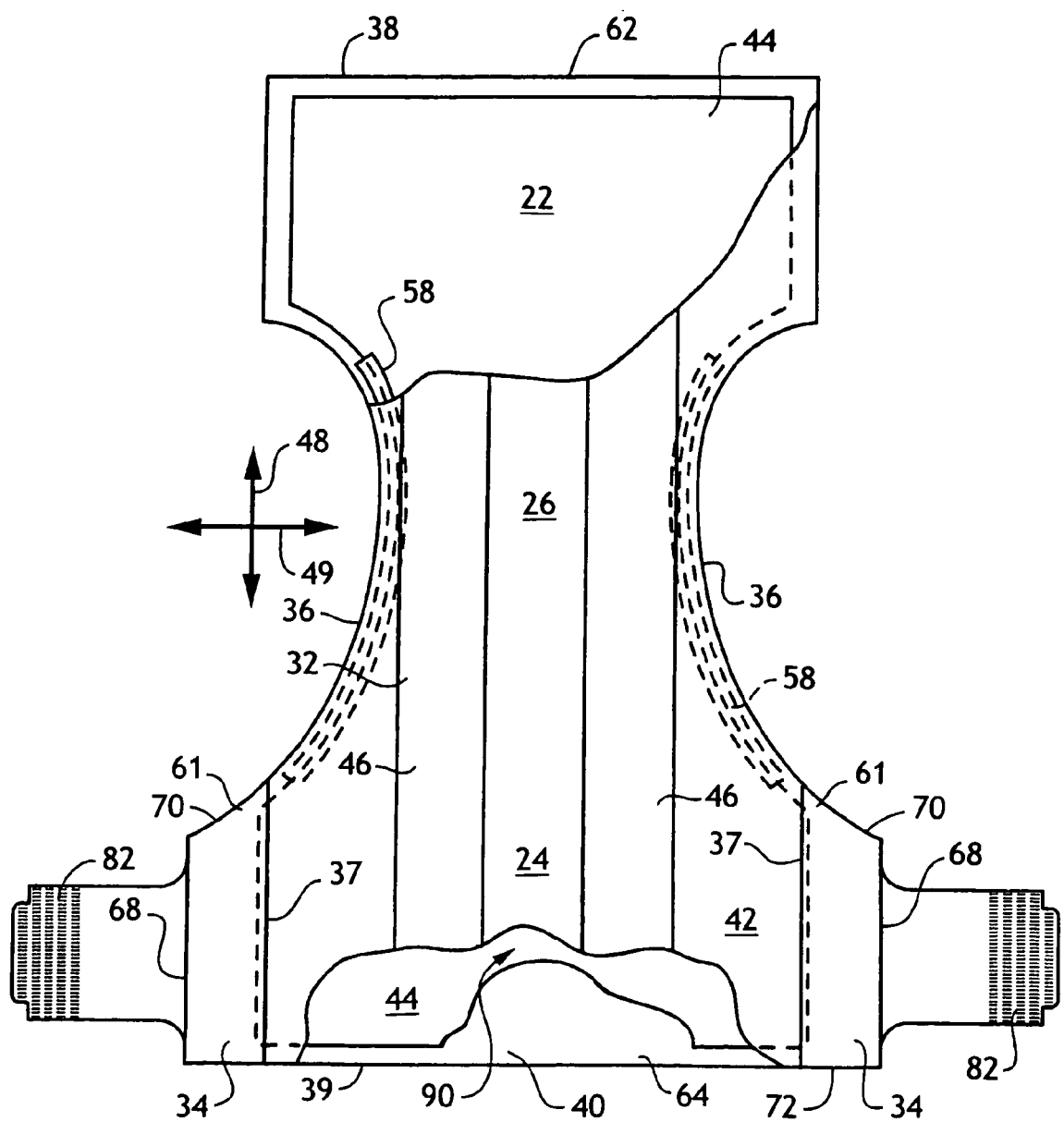
FIG. 4 is a plan view similar to FIG. 3 showing the surface of the absorbent article that faces the wearer when worn and with portions cut away to show underlying features.

A diaper 20 is representatively illustrated in FIG. 1 in a partially fastened condition. The diaper 20 shown in FIGS. 1 and 2 is also represented in FIGS. 3 and 4 in an opened and unfolded state. Specifically, FIG. 3 is a plan view illustrating the exterior side of the diaper 20, while FIG. 4 illustrates the interior side of the diaper 20. As shown in FIGS. 3 and 4, the diaper 20 defines a longitudinal direction 48 that extends from the front of the article when worn to the back of the article. Opposite to the longitudinal direction 48 is a lateral direction 49.

The diaper 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The diaper 20 also defines an inner surface 28 adapted in use (e.g., positioned relative to the other components of the article 20) to be disposed toward the wearer, and an outer surface 30 opposite the inner surface. The front and back regions 22, 24 are those portions of the diaper 20 which, when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated diaper 20 includes a chassis 32 that, in this aspect, encompasses the front region 22, the back region 24, and the crotch region 26. Referring to FIGS. 1-4, the chassis 32 includes an outer cover 40 and a bodyside liner 42 (FIGS. 1 and 4) that may be joined to the outer cover 40 in a superimposed relation therewith by adhesives, ultrasonic bonds, thermal bonds or other conventional techniques. Referring to FIG. 4, the liner 42 may suitably be joined to the outer cover 40 along the perimeter of the chassis 32 to form a front waist seam 62 and a back waist seam 64. As shown in FIG. 4, the liner 42 may suitably be joined to the outer cover 40 to form a pair of side seams 61 in the front region 22 and the back region 24. The liner 42 can be generally adapted, i.e., positioned relative to the other components of the article 20, to be disposed toward the wearer's skin during wear of the absorbent article. The chassis 32 may further include an absorbent structure 44 particularly shown in FIG. 4 disposed between the outer cover 40 and the bodyside liner 42 for absorbing liquid body exudates from the wearer, and may further include a pair of containment flaps 46 secured to the bodyside liner 42 for inhibiting the lateral flow of body exudates.

The elasticized containment flaps 46 as shown in FIG. 4 define a partially unattached edge which assumes an upright configuration in at least the crotch region 26 of the diaper 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art.

To further enhance containment and/or absorption of body exudates, the diaper 20 may also suitably include leg elastic members 58 (FIG. 4), as are known to those skilled in the art. The leg elastic members 58 can be operatively joined to the outer cover 40 and/or the bodyside liner 42 and positioned in the crotch region 26 of the absorbent article 20. The leg elastic members 58 can be formed of any suitable elastic material.

In some aspects, the absorbent article 20 may further include a surge management layer 60 that may be optionally located adjacent the absorbent structure 44 and attached to various components in the article 20, such as the absorbent structure 44 or the bodyside liner 42, by methods known in the art, such as by using an adhesive. A surge management layer 60 helps to decelerate and diffuse surges or gushes of liquid that may be rapidly introduced into the absorbent structure of the article. Desirably, the surge management layer 60 can rapidly accept and temporarily hold the liquid prior to releasing the liquid into the storage or retention portions of the absorbent structure.

As shown in FIGS. 1-4, the absorbent article 20 further includes a pair of opposing elastic side panels 34 that are attached to the back region of the chassis 32. As shown particularly in FIGS. 1 and 2, the side panels 34 may be stretched around the waist and/or hips of a wearer in order to secure the garment in place. As shown in FIGS. 3 and 4, the elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative aspect, the elastic side panels may also be integrally formed with the chassis 32. For instance, the side panels 34 may comprise an extension of the bodyside liner 42, of the outer cover 40, or of both the bodyside liner 42 and the outer cover 40.

In the aspects shown in the figures, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIGS. 1 and 2, the elastic side panels 34 may be connected by a fastening system 80 to define a 3-dimensional diaper configuration having a waist opening 50 and a pair of leg openings 52. The waist opening 50 of the article 20 is defined by the waist edges 38 and 39 which encircle the waist of the wearer.

In the aspects shown in the figures, the side panels are releasably attachable to the front region 22 of the article 20 by the fastening system. It should be understood, however, that in other aspects, the side panels may be permanently joined to the chassis 32 at each end. The side panels may be permanently bonded together, for instance, when forming a training pant or absorbent swimwear.

The elastic side panels 34 each have a longitudinal outer edge 68, a leg end edge 70 disposed toward the longitudinal center of the diaper 20, and waist end edges 72 disposed toward a longitudinal end of the absorbent article. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present disclosure. As shown in FIG. 4, the outer edges 68 are generally parallel to the longitudinal direction 48 while the waist end edges 72 are generally parallel to the transverse axis 49. It should be understood, however, that in other aspects the outer edges 68 and/or the waist edges 72 may be slanted or curved as desired. Ultimately, the side panels 34 are generally aligned with a waist region 90 of the chassis.

The fastening system 80 may include laterally opposite first fastening components 82 adapted for refastenable engagement to corresponding second fastening components 84. In the aspect shown in the figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration. The fastening components 82, 84 may be any refastenable fasteners suitable for absorbent articles.

In the aspect shown in the figures, the fastening components 82 are attached to the side panels 34 along the edges 68. In this aspect, the fastening components 82 are not elastic or extendable. In other aspects, however, the fastening components may be integral with the side panels 34. For example, the fastening components may be directly attached to the side panels 34 on a surface thereof.

In addition to possibly having elastic side panels, the absorbent article 20 may include various waist elastic members for providing elasticity around the waist opening. For example, as shown in the figures, the absorbent article 20 can include a front waist elastic member 54 and/or a back waist elastic member 56.

The materials used to form the absorbent article 20 that surround the waist elastic members 54 and 56 may vary depending upon the particular application and the particular product being produced.

The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded-carded webs or foams provided by elastomeric or polymeric materials. The outer cover 40, for instance, can be a single layer of a liquid impermeable material, or alternatively can be a multi-layered laminate structure in which at least one of the layers is liquid impermeable. In other aspects, however, it should be understood that the outer cover may be liquid permeable. In this aspect, for instance, the absorbent article may contain an interior liquid barrier layer.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44.

The absorbent structure 44 may be disposed between the outer cover 40 and the bodyside liner 42. The absorbent structure 44 can be any structure or combination of components which are generally compressible, conformable, non-irritating to a wearer's skin, and capable of absorbing and retaining liquids and certain body wastes. As a general rule, superabsorbent material is present in the absorbent web in an amount of from about 0 to about 90 weight percent based on total weight of the web. Superabsorbent materials are well known in the art.

After being formed or cut into a desired shape, the absorbent web material may be wrapped or encompassed by a suitable tissue or meltblown web or the like wrap sheet that aids in maintaining the integrity and shape of the absorbent structure 44. The absorbent web material may also be a coform material.

Referring to FIG. 2 for exemplary purposes, a signaling device 110 is shown attached to the absorbent article 20. The signaling device 110 includes a detection circuit 120 as described below. When a body exudate is present in the absorbent article 20, the detection circuit 120 detects the presence of the body exudate and activates the signaling device 110. The signaling device 110 can be a single unit removably attached to or held in the vicinity of the absorbent article 20. In another aspect of the present disclosure (not shown), the signaling device 110 can include a transmitter and a receiver. In particular, in one aspect of the present disclosure, the transmitter sends a wireless signal to the receiver which then indicates to a wearer or caregiver that a body exudate is present in the absorbent article 20. Further details on this aspect can be obtained in, for example, in U.S. Patent Application Publication No. 2006/0244614 to Long and entitled "Connection Mechanisms," which is incorporated herein by reference to the extent it is consistent (i.e., not in conflict) herewith.

The signaling device 110 can emit an audible signal or a visual signal to indicate to the user that a body exudate is present in the absorbent article 20. The audible signal, for instance, may be as simple as one or more beeps or may emit a musical tune. Similarly, if the signaling device 110 issues a visible signal, the visible signal may comprise one light, multiple lights, or an interactive display. In still another aspect of the present disclosure, the receiver of the signaling device 110 may be configured to vibrate when the circuit within the wetness sensing absorbent article is activated.

In the aspect of the present disclosure shown in FIG. 1, the signaling device 110 is a single unit that remains attached to or that is adapted to be held in the vicinity of the absorbent article 20. For example, the signaling device may be mounted on the absorbent article 20 and issue a visible signal and/or an audible signal from the article itself.

In various aspects of the present disclosure, the absorbent article 20 may include additional features such as those disclosed in co-pending and co-assigned U.S. patent application Ser. No. 11/303,283 to Long, et al. and entitled "Garments With Easy-To-Use Signaling Device"; and U.S. patent application Ser. No. 11/215,937 to Ales, et al. and entitled "Method of Detecting the Presence of an Insult in an Absorbent Article and Device for Detecting the Same"; which are incorporated herein by reference to the extent they are consistent (i.e., not in conflict) herewith. For example, the absorbent article 20 may also include other wetness sensing features such as fading ink, appearing ink, a wetness liner, or a cooling component.

The absorbent article 20 may be a part of a wetness sensing or body exudate indicating system such as those described in co-pending and co-assigned U.S. patent application Ser. No. 11/414,032, filed on Apr. 27, 2006, by Allen, et al. and entitled "An Array of Wetness Sensing Articles."

In various aspects of the present disclosure, the absorbent article 20 may be configured to be used in toilet training a child, in addressing enuresis in a subject, or in monitoring incontinence in a subject, particularly an adult. In one aspect of the present disclosure, each signaling device manufactured and sold will be compatible with every wetness sensing absorbent article manufactured and sold for any application.

Figure 5:
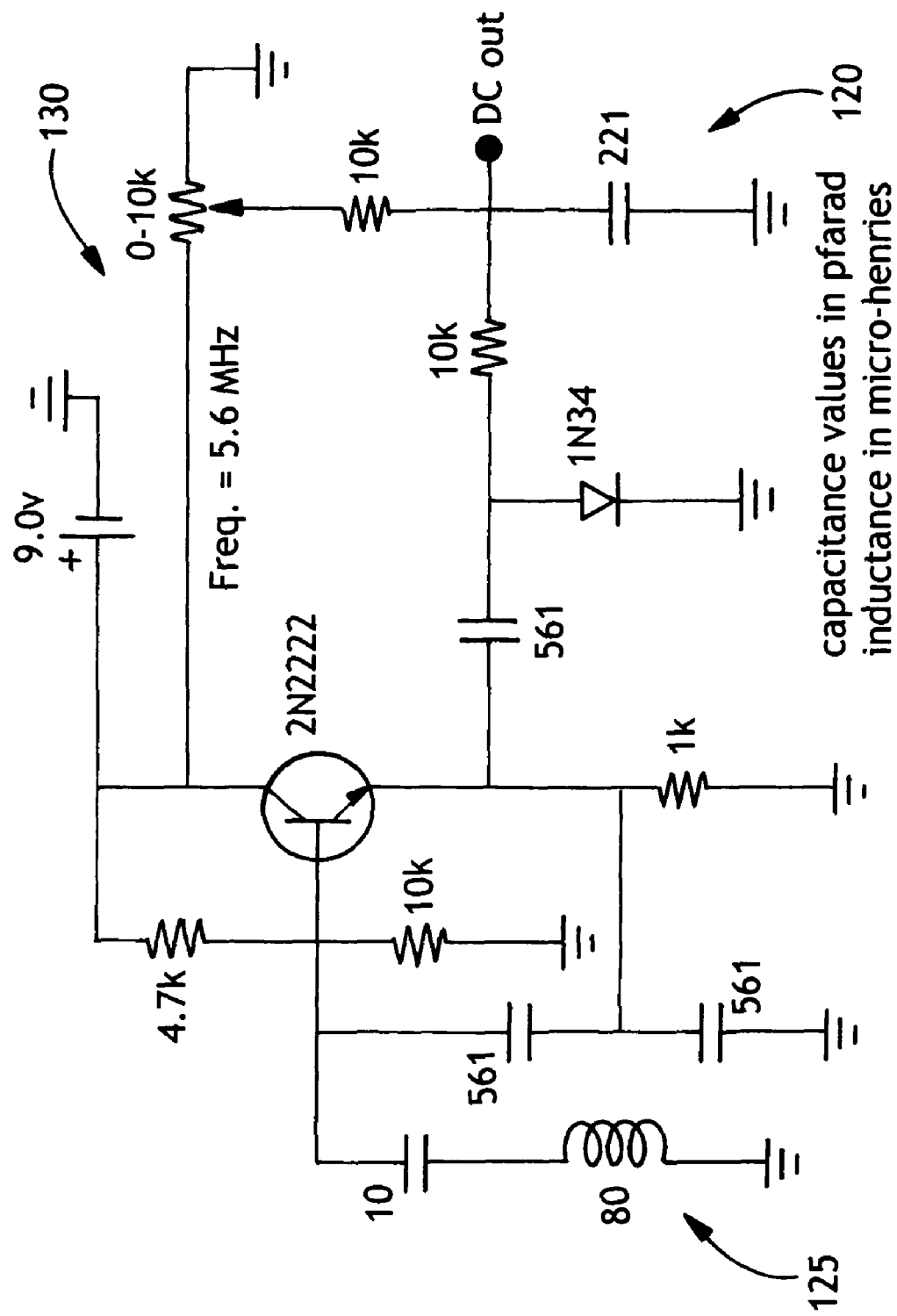
FIG. 5 is a schematic diagram of one aspect of the disclosure including an induction coil and a marginal oscillator circuit.

In one aspect of the present disclosure illustrated in FIG. 5, the signaling device 110 includes a detection circuit 120 that is adapted to detect the presence of a body exudate in the absorbent article 20. The detection circuit includes an induction coil 125 that, when placed in the vicinity of a conductive liquid such as urine, will generate weak electrical eddy currents in the liquid. The electrical currents in turn generate a field that couples with the induction coil 125, changing its impedance—both real and imaginary parts.

Induction coils 125 can be made as small as having a diameter of about 1.0 mm, although the field of view of the induction coil 125 is reduced as the size of the coil 125 is reduced. Induction coils 125 can also be made large to increase the field of view, with diameters as large as 10 cm, but larger induction coils 125 can become impractical for use with absorbent article applications. Although induction coils 125 of any size can be used, coils 125 in the range of about 0.5 cm to about 8 cm are more practical. Likewise, coils 125 in the range of about 1 cm to about 5 cm have additional advantages. Finally, coils 125 in the range of about 1 cm to about 2 cm have the most practicality.

The detection circuit 120 also includes a marginal oscillator circuit 130. The marginal oscillator circuit 130 is used to detect the altered impedance of the induction coil 125. An example of such an oscillator circuit 130 is illustrated in FIG. 5. The marginal oscillator circuit 130, in its simplest form, is a standard Colpitts-type oscillator that has just barely enough feedback to drive it into oscillation. In other aspects of the present application, the oscillator can be any suitable oscillator circuit including a Franklin or a Hartley oscillator. When conductive objects are brought close to the induction coil 125, energy is removed from the oscillator due to ohmic losses in the conductive object. This removal of energy registers in the oscillator's output, which in this case can be interpreted to measure either the amount of conductive liquid in the absorbent article or the liquid's conductivity. Once the device is activated, the processor takes a baseline measurement, which is automatic and transparent to the user. Once the signaling device 110 is installed by a user, the detection circuit 120 automatically zeroes itself to establish the point of zero wetness baseline needed.

The electronics associated with the detection circuit 120 are relatively simple and can be miniaturized to postage stamp size. The detection circuit 120 includes the induction coil 125, which in one example includes about 40 turns of #36 wire formed into a planar loop about 2 cm in diameter.

The complete detection circuit 120 is disposed in a housing 135 (see FIGS. 2 and 6) that is adapted to be attached to the absorbent article 20, or held in vicinity to the absorbent article 20. If the housing 135 is to be attached to the absorbent article 20 using an attachment mechanism 140, the housing 135 can be a pouch or a rigid or semi-rigid housing 135 that attaches to the outer cover 40 of the absorbent article 20 near the region where insults are expected. Such attachment mechanism 140 can use adhesive, hook and loop, mechanical fasteners such as snaps, a clip, or a clasp, any other suitable attachment mechanism, or any combination of these. Various attachment mechanisms 140 include those disclosed in co-pending and co-assigned U.S. Patent Application Publication No. 2007/0142797 to Long, et al. and entitled "Garments With Easy-To-Use Signaling Device"; U.S. Patent Application Publication No. 2006/0244614 to Long and entitled "Connection Mechanisms"; and U.S. Patent Application Publication No. 2007/0024457 to Long, et al. and entitled "Connection Mechanisms In Absorbent Articles For Body Fluid Signaling Devices" which are incorporated herein by reference to the extent they are consistent (i.e., not in conflict) herewith.

In another aspect of the present invention, the signaling device 110 is adapted to be held in near the outermost surface of the outer cover 40 of the absorbent article 20. In this aspect, no attachment mechanism 138 is needed. The wearer of the absorbent article 20 or a caregiver holds the signaling device 110 near the outer cover 40 of the absorbent article 20 to detect whether the absorbent article 20 has received an insult.

After the absorbent article 20 has received a first insult, the signal from the marginal oscillator circuit 130 rises to a relatively high level while superabsorbent swelling occurs, but then reaches a plateau as liquid is wicked away from the field of view of the induction coil 125. The field of view of the induction coil 125 is the region in which an insult will affect the induction coil 125. Thus, an abrupt rise in the signal output of the marginal oscillator circuit 130 followed by a leveling is expected. In the absence of superabsorbent, the signal would slowly fall in response to wicking. A second insult to the absorbent article 20 produces an abrupt drop in signal since incoming urine is usually less conductive than swollen superabsorbent. After the second insult is complete, the signal begins to rise again, but to values that are higher than those following the first insult, but ultimately followed again by a period of decay if superabsorbent levels are small. When the detector circuit 120 detects an insult, the signaling device 110 provides a signal to the wearer or to the caregiver as described above.

In some instances, it is conceivable that the detection circuit 120 needs to contend with nearby conductive objects that can cause interference. In practical applications, however, such a situation is unlikely because the interference-causing conductive object typically needs to be within one coil diameter of the coil's center. This makes the appearance of an interference-causing conductive object unlikely within one coil diameter of the center of the induction coil when the detection circuit 120 is used in conjunction with an absorbent article 20. Nevertheless, an interference problem of this sort can be managed by an intelligent processor that recognizes and stores signal output once the induction coil 125 is in position and activated. The processor uses this signal output as a reference point and interprets subsequent signals in relation to this reference point. In other words, the processor includes an intelligent zeroing feature.

In another aspect of the present disclosure (not shown), the signaling device 110 uses more than one induction coil 125. For example, two induction coils 125 can be positioned such that one is near the front of the absorbent article 20 to detect urine and the other is near the rear of the absorbent article 20 to detect fecal matter.

Figure 6:
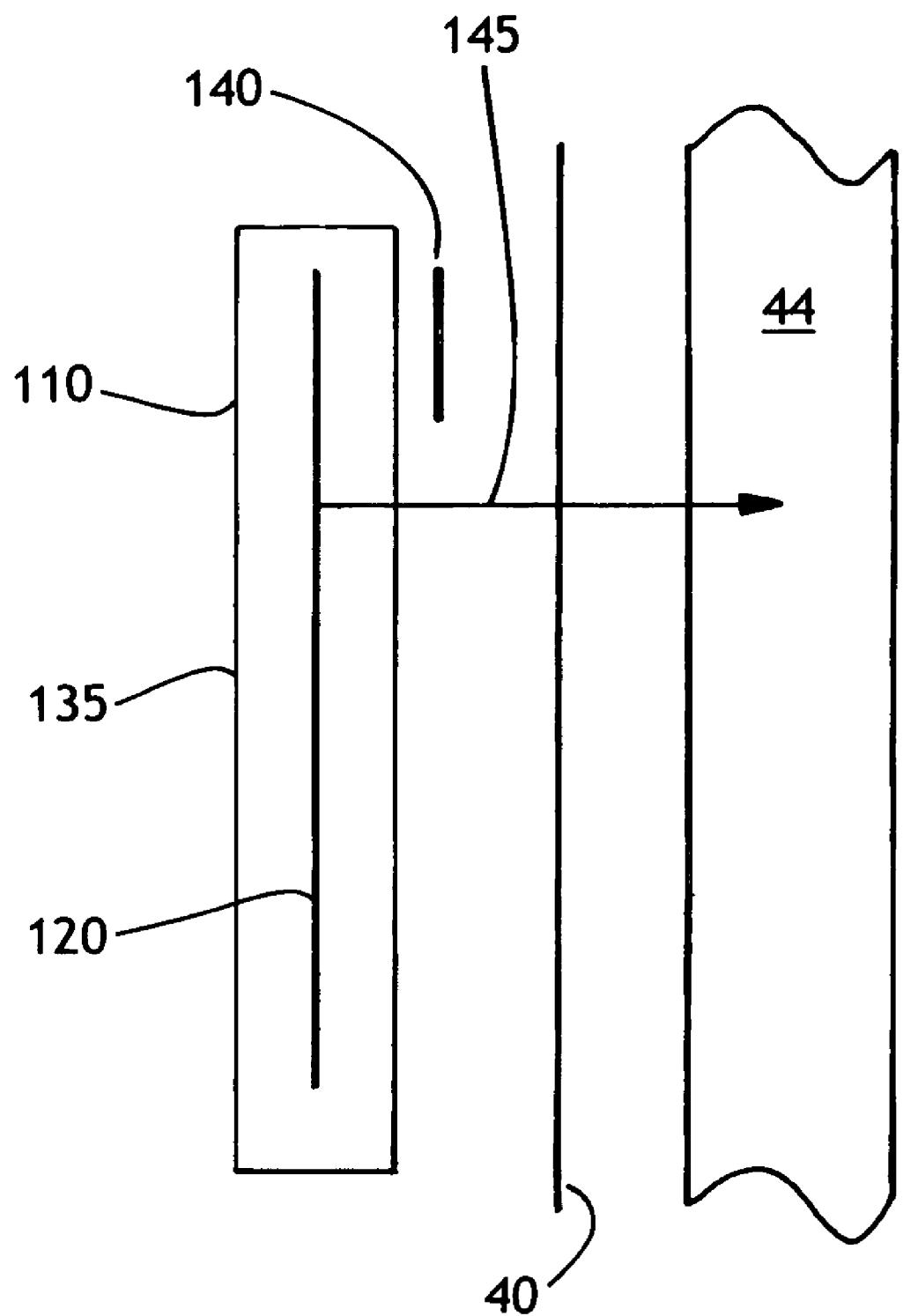
FIG. 6 is a cutaway exploded side view elevation schematic of another aspect of the disclosure including a signaling device with a grounding lead.

In another aspect of the present disclosure illustrated in FIG. 6, a grounding lead 145 between the electrical common of the signaling device 110 and the absorbent structure 44 can be used to ensure that the signaling device 110 and the liquid in the absorbent structure 44 are at the same potential or voltage. Such a grounding lead 145 can help the detector circuit 120 to be more sensitive to sensing impedance changes in the induction coil 125 as such a grounding lead arrangement can reduce noise in the system. The grounding lead arrangement can be accomplished by any suitable means of providing a conductor between the electrical common of the signaling device 110 and the absorbent structure 44. For example, a conductive means for attaching the signaling device 110 to the absorbent article 20 such as a snap, a clasp, or a clip can be used as the grounding lead 145. In another example, a wire or spike protruding from the side of the signaling device 110 facing the absorbent article 20 can pierce the outer cover 40 to contact the absorbent structure 44, thus providing a conductive grounding lead 145 between the electrical common of the signaling device 110 and the absorbent structure 44. In other words, in these aspects there is a grounding lead mechanism between the electrical common of the signaling device 110 and the absorbent structure 44 to equalize the potential between the target liquid and the electrical common of the signaling device 110.

These and other modifications and variations to the present disclosure may be practiced by those of ordinary skill in the art, without departing from the spirit and scope of the present disclosure, which is more particularly set forth in the appended claims. In addition, it should be understood that aspects of the various aspects may be interchanged both in whole or in part. Furthermore, those of ordinary skill in the art will appreciate that the foregoing description is by way of example only, and is not intended to limit the disclosure so further described in such appended claims.

What is claimed is:

1. A signaling device for sensing and indicating the presence of a body exudate in an absorbent article having an outer cover, the device comprising:
    a housing;
    a detection circuit disposed within the housing, the detection circuit including an induction coil and a marginal oscillator; and
    a grounding lead adapted to pierce the outer cover of the absorbent article.

2. The device of claim 1, further comprising an attachment mechanism for removably attaching the device to the absorbent article.

3. The device of claim 2, wherein the detection circuit has an electrical common, and wherein the attachment mechanism is in electrical communication with the electrical common and with the body exudate.

4. The device of claim 1, further comprising a grounding means for equalizing the potential between the detection circuit and the body exudate.

5. The device of claim 1, wherein the detection circuit has an electrical common, and further comprising a conductor in electrical communication with the electrical common and with the body exudate.

6. The device of claim 1, wherein the housing is flexible.

7. The device of claim 1, wherein the induction coil comprises a spiral coil.

8. The device of claim 1, wherein the signaling device is adapted to provide notification of the presence of a body exudate in the absorbent article.

9. The device of claim 8, wherein the signaling device is adapted to provide a visual notification.

10. The device of claim 8, wherein the signaling device is adapted to provide an audio notification.

11. The device of claim 8, wherein the signaling device is adapted to provide a wireless notification.

12. The device of claim 8, wherein the signaling device is adapted to provide a vibratory notification.

13. The device of claim 1, wherein the device is adapted to be held adjacent the absorbent article.

14. A body exudate collection and detection system comprising:
    an absorbent article having an outer cover;
    a signaling device adapted to be used in conjunction with the absorbent article, the signaling device including a housing and a detection circuit disposed within the housing, the detection circuit including an induction coil and a marginal oscillator; and
    a grounding lead adapted to pierce the outer cover of the absorbent article.

15. The system of claim 14, further comprising an attachment mechanism for removably attaching the signaling device to the absorbent article.

16. The device of claim 14, further comprising a grounding means for equalizing the potential between the detection circuit and the body exudate.

17. The device of claim 14, wherein the signaling device is adapted to provide notification of the presence of a body exudate in the absorbent article.

18. The device of claim 14, wherein the device is adapted to be held adjacent the absorbent article.

19. A signaling device for sensing and indicating the presence of a body exudate in an absorbent article having an outer cover, the device comprising:
    a housing;
    an attachment mechanism for removably attaching the housing to the absorbent article;
    a detection circuit disposed within the housing, the detection circuit including an induction coil, a marginal oscillator, an electrical common, and a conductor in electrical communication with the electrical common and with the body exudate; and
    a grounding lead adapted to pierce the outer cover of the absorbent article.

* * * * *